US00PP36157P2

(12) United States Plant Patent
Heuger

(10) Patent No.: US PP36,157 P2
(45) Date of Patent: Sep. 24, 2024

(54) ***HELLEBORUS* PLANT NAMED 'HER 1210'**

(50) Latin Name: ***Helleborus ericsmithii* X *Helleborus* x *hybridus***
Varietal Denomination: HER 1210

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 18/389,494

(22) Filed: Nov. 14, 2023

(51) Int. Cl.
*A01H 5/02* (2018.01)
*A01H 6/72* (2018.01)

(52) U.S. Cl.
USPC ..... Plt./439
CPC ..... *A01H 6/72* (2018.05)

(58) Field of Classification Search
USPC ..... Plt./439
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Helleborus* plant named 'HER 1210', characterized by its upright to somewhat outwardly spreading and mounded plant habit; vigorous growth habit; dark green-colored leaflets with lighter green-colored venation; freely flowering habit; whitish green-colored flowers that are tinged with purplish pink; and good garden performance.

1 Drawing Sheet

Figure 1:
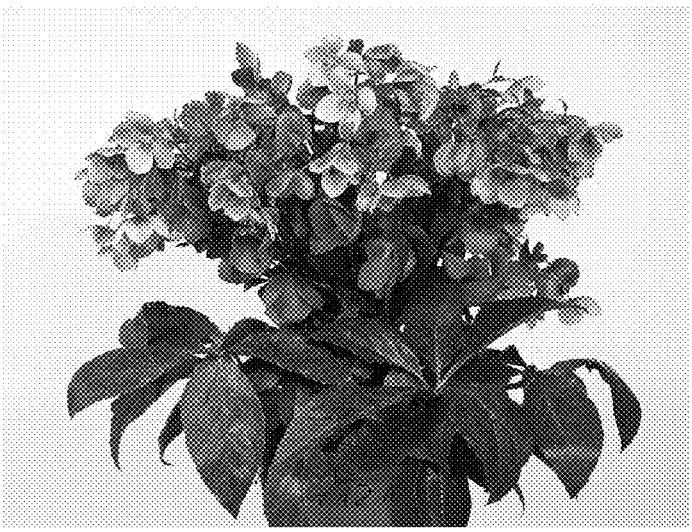

Botanical designation: *Helleborus ericsmithii* X *Helleborus* x *hybridus.*
Cultivar denomination: 'HER 1210'.

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Jun. 20, 2023, application number 2023/1369. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus ericsmithii* X *Helleborus* x *hybridus* and hereinafter referred to by the name 'HER 1210'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stresses.

The new *Helleborus* plant originated from a cross-pollination conducted by the Inventor in Glandorf, Germany in December, 2013 of a proprietary selection of *Helleborus ericsmithii* identified as code number P547, not patented, as the female, or seed, parent and a proprietary selection of *Helleborus* x *hybridus* identified as code number HO1456, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in November, 2015.

Asexual reproduction of the new *Helleborus* plant by in vitro axillary meristem culture in a controlled environment in Glandorf, Germany since April, 2016 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HER 1210'. These characteristics in combination distinguish 'HER 1210' as a new and distinct *Helleborus* plant:

1. Upright to somewhat outwardly spreading and mounded plant habit.
2. Vigorous growth habit.
3. Dark green-colored leaflets with lighter green-colored venation.
4. Freely flowering habit.
5. Whitish green-colored flowers that are tinged with purplish pink.
6. Good garden performance.

Plants of the new *Helleborus* differ from plants of the female parent selection in the following characteristics:

1. Leaflets of plants of the new *Helleborus* are darker green in color than leaflets of plants of the female parent selection.
2. Flowers of plants of the new *Helleborus* are whitish green in color tinged with purplish pink whereas flowers of plants of the female parent selection are creamy white in color.

Plants of the new *Helleborus* differ from plants of the male parent selection in the following characteristics:

1. Leaflets of plants of the new *Helleborus* are darker green in color than leaflets of plants of the male parent selection.
2. Flowers of plants of the new *Helleborus* are whitish green in color tinged with purplish pink whereas flowers of plants of the male parent selection are pink in color.

Plants of the new *Helleborus* can also be compared to plants of *Helleborus* x *ericsmithii* X *Helleborus* x *hybridus* 'COSEH 4800', disclosed in U.S. Plant Pat. No. 31,182. In side-by-side comparisons, plants of the new *Helleborus* differ primarily from plants of 'COSEH 4800' in the following characteristics:

1. Leaflets of plants of the new *Helleborus* are smaller than leaflets of plants of 'COSEH 4800'.
2. Flowers of plants of the new *Helleborus* are whitish green in color tinged with purplish pink whereas flowers of plants of 'COSEH 4800' are greyed purple in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph at the top of the sheet (FIG. 1) is a side perspective view of a typical flowering plant of 'HER 1210' grown in a container.

Figure 2:
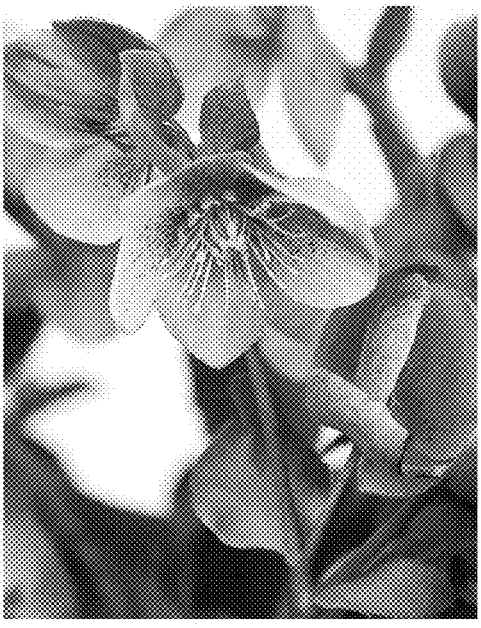

The photograph at the bottom of the sheet (FIG. 2) is a close-up view of a typical flowering plant of 'HER 1210'.

DETAILED BOTANICAL DESCRIPTION

The aforementioned photographs and following observations, measurements and values describe plants grown during the early spring in 15-cm containers in a glass-covered greenhouse in Glandorf, Germany and under cultural practices typical of commercial *Helleborus* production. During the production of the plants, day temperatures ranged from 12 C to 20 C and night temperatures ranged from 5 C to 12 C. Plants were 48 weeks old when the photographs were taken and twelve months old when the description was taken. In the following description, color references are made to The Royal Horticultural Society Colour Chart, 2015 Edition, except where general terms of ordinary dictionary significance are used.

Botanical classification: *Helleborus ericsmithii* X *Helleborus* x *hybridus* 'HER 1210'.

Parentage:

*Female, or seed, parent*.—Proprietary selection of *Helleborus ericsmithii* identified as code number P547, not patented.

*Male, or pollen, parent*.—Proprietary selection of *Helleborus* x *hybridus* identified as code number HO1456, not patented.

Propagation:

*Type*.—In vitro axillary meristem culture.

*Time to initiate roots, winter*.—About 55 days at temperatures about 12 C.

*Time to produce a rooted young plant, winter*.—About 170 days at temperatures ranging from about 4 C to 15 C.

*Root description*.—Thick to thin, fleshy; typically white to brownish in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to somewhat outwardly spreading and mounding plant habit with flowers held within and slightly above the foliar plane; plant shape, roughly flattened globular; vigorous growth habit and moderate to rapid growth rate.

*Plant height, soil level to top of foliar plane*.—About 15.2 cm.

*Plant height, soil level to top of flowers*.—About 33.5 cm.

*Plant diameter* (*area of spread*).—About 62.8 cm.

Leaf description:

*Arrangement*.—Leaves arranged in a basal rosette; leaves palmately compound with typically five leaflets per leaf.

*Leaf length*.—About 26.1 cm.

*Leaf width*.—About 34.3 cm.

*Leaflet length*.—About 18.3 cm.

*Leaflet width*.—About 7.4 cm.

*Leaf shape*.—Palmate; roughly reniform in outline.

*Leaflet shape*.—Slightly obovate to elliptic.

*Leaflet apex*.—Acute.

*Leaflet base*.—Attenuate.

*Leaflet margin*.—Serrate; slightly to moderately coarsely undulate.

*Leaflet texture and luster, upper surface*.—Smooth, glabrous; coriaceous and tough; moderately glossy.

*Leaflet texture and luster, lower surface*.—Smooth, glabrous; coriaceous and tough; matte.

*Leaflet venation pattern*.—Pinnate and reticulate.

*Leaflet color*.—Developing leaflets, upper surface: Close to 146A; towards the base, tinged with close to 177C. Developing leaflets, lower surface: Close to 148A slightly tinged with close to 200C; midvein, close to 187A. Fully developed leaflets, upper surface: Slightly darker than a blend of 139A and N189A; towards the base, tinged with close to N199B; venation, close to 144A and 144B and towards the base, close to 195A. Fully developed leaflets, lower surface: Close to 191A; venation, close to 177A.

*Petioles*.—Length: About 14.1 cm. Diameter: About 6 mm by 6 mm. Strength: Strong. Texture and luster, upper and lower surfaces: Smooth, glabrous; moderately glossy. Color, upper surface: Close to 146A; heavily covered with fine dots, close to 200B. Color, lower surface: Close to 146A; heavily covered with fine dots, close to 200B and 166A.

Flower description:

*Flower shape and habit*.—Single rotate bowl-shaped flowers arranged in panicles; freely flowering habit with about 23 flowers per inflorescence and about 180 flowers and flower buds per plant; flowers face mostly outwardly to nodding.

*Fragrance*.—None detected.

*Natural flowering season*.—Plants begin flowering about ten months after planting; plants flower naturally during the late winter in Germany.

*Flower longevity on the plant*.—About ten days; sepals persistent, other flower parts are not persistent.

*Flower buds*.—Length: About 2 cm. Diameter: About 1.3 cm. Shape: Ovate. Texture and luster: Smooth, glabrous; matte. Color: Close to 145C tinged with close to 182B.

*Inflorescence height* (*including peduncle*).—About 32.5 cm.

*Inflorescence diameter*.—About 37.8 cm.

*Flower diameter*.—About 5.3 cm.

*Flower depth*.—About 2.3 cm.

*Petals*.—All petals are transformed into nectaries.

*Sepals*.—Quantity and arrangement: About five, arranged in a single whorl. Length: About 3.5 cm. Width: About 2.7 cm. Shape: Broadly ovate to broadly elliptic; moderately concave. Apex: Broadly and bluntly acute to obtuse. Base: Cuneate. Margin: Entire; coarsely undulate. Texture and luster, upper surface: Smooth, glabrous; matte. Texture and luster, lower surface: Smooth, glabrous; slightly glossy. Color: When opening, upper surface: Close to 155B and 155C slightly tinged with close to 186D; towards the apex, close to 157A; towards the base, close to 145B; base, marbled, striped and dotted with close to 185A to 185C. When opening, lower surface: Close to 155B to 155C and 145C slightly tinged with close to 186C; towards the base, close to 145A. Fully opened, upper surface: Close to 157A and 145C slightly tinged with close to 186D; towards the base, close to 146C; proximally, marbled, striped and dotted with close to 187A and 187B; venation, similar to lamina colors; color does not change with subsequent development. Fully opened, lower surface: Close to 155A to 155C, 145C and 177C tinged with close to 183D; towards the base, close to 146C; proximally, slightly marbled, striped and dotted with close to 187B; venation, similar to lamina colors; color does not change with subsequent development.

*Flower bracts*.—Quantity per flower: Typically two. Length: About 5.4 cm. Width: About 3.1 cm. Shape: Ovate to broadly ovate. Apex: Acute. Base: Truncate to cuneate. Margin: Serrate; slightly coarsely undulate. Color, upper surface: Close to a blend of NN137A and 147A; towards the base, close to 138A. Color, lower surface: Close to a blend of 147A and 191A; venation, close to 166A.

*Peduncles*.—Length: About 23.9 cm. Diameter: About 7 mm to 8 mm. Aspect: About 20 degrees from vertical. Strength: Strong. Texture and luster: Smooth, glabrous; moderately glossy. Color: Close to 146C; heavily covered with fine dots, close to 183A.

*Pedicels*.—Length: About 3.6 cm. Diameter: About 1.5 mm. Aspect: About 30 degrees from peduncle axis. Strength: Moderately strong. Texture and luster: Sparsely pubescent; slightly glossy. Color: Close to 144C.

*Reproductive organs*.—Stamens: Quantity per flower: About 30. Filament length: About 1.6 cm. Filament color: Close to 145C and 145D. Anther shape: Double and broadly reniform; basifixed. Anther size: About 1.5 mm by 2 mm. Anther color: Close to 154D. Pollen amount: Sparse. Pollen color: Close to 4D to lighter than 4D. Pistils: Quantity per flower: About five to six. Pistil length: About 1.3 cm. Stigma diameter: About 0.3 mm. Stigma shape: Club-shaped. Stigma color: Close to 153B. Style length: About 1.25 cm. Style color: Close to 177B. Ovary color: Close to 144B. Nectaries (transformed petals): Quantity per flower: About 11 to 13. Length: About 9 mm. Diameter: About 2.5 mm. Shape: Tubular, flattened; apices, obtuse. Texture and luster, inner and outer surfaces: Smooth, glabrous; slightly glossy. Color, immature, inner and outer surfaces: Close to 144A; towards the apex, close to 145A. Color, mature, inner and outer surfaces: Close to N144A; towards the apex, close to 151B; towards the base, close to 152C; color does not change with subsequent development.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35 C and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'HER 1210' as illustrated and described.

* * * * *